United States Patent
Griffin et al.

(10) Patent No.: US 8,512,566 B2
(45) Date of Patent: Aug. 20, 2013

(54) DISPOSABLE FLUID PATH SYSTEMS AND METHODS FOR PROCESSING COMPLEX BIOLOGICAL MATERIALS

(75) Inventors: Weston Blaine Griffin, Niskayuna, NY (US); Jaydeep Roy, Saratoga Springs, NY (US); Eric Douglas Williams, Duanesburg, NY (US); Philip Alexander Shoemaker, Scotia, NY (US); James Mitchell White, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 734 days.

(21) Appl. No.: 12/636,112

(22) Filed: Dec. 11, 2009

(65) Prior Publication Data
US 2011/0139723 A1  Jun. 16, 2011

(51) Int. Cl.
*B01D 35/00* (2006.01)
*B01D 21/00* (2006.01)
B01D 63/08 (2006.01)
B01D 21/30 (2006.01)
A61M 1/34 (2006.01)
A61M 1/38 (2006.01)

(52) U.S. Cl.
USPC ....... 210/312; 210/295; 210/500.23; 210/134

(58) Field of Classification Search
None
See application file for complete search history.

(56) References Cited

U.S. PATENT DOCUMENTS

| 3,576,650 | A | * | 4/1971 | Underwood | 206/484 |
|---|---|---|---|---|---|
| 4,276,175 | A | * | 6/1981 | Bower | 210/636 |
| 5,055,198 | A | * | 10/1991 | Shettigar | 210/650 |
| 5,162,102 | A | | 11/1992 | Nogawa et al. | |
| 5,876,611 | A | * | 3/1999 | Shettigar | 210/739 |
| 6,174,447 | B1 | * | 1/2001 | Spindler | 210/745 |
| 6,695,803 | B1 | * | 2/2004 | Robinson et al. | 604/4.01 |
| 2002/0161322 | A1 | * | 10/2002 | Utterberg et al. | 604/6.16 |
| 2004/0195178 | A1 | * | 10/2004 | Carpenter et al. | 210/645 |
| 2006/0054557 | A1 | | 3/2006 | Hori et al. | |
| 2007/0175825 | A1 | * | 8/2007 | Denney | 210/631 |
| 2008/0220523 | A1 | | 9/2008 | Antwiler | |

FOREIGN PATENT DOCUMENTS
WO  WO2008090406 A2  7/2008

OTHER PUBLICATIONS

Co-pending US Patent Application entitled "Systems and Methods for Processing Complex Biological Materials", U.S. Appl. No. 12/325,672, filed Dec. 8, 2008.

* cited by examiner

*Primary Examiner* — Katherine Zalasky
(74) *Attorney, Agent, or Firm* — Eileen B. Gallagher

(57) ABSTRACT

Disclosed herein is a disposable fluid path for processing complex materials. The disposable fluid path comprises a gravity assisted disposable system for separating a biological sample into two or more distinct submaterials through sedimentation. The fluid path is comprised of a sample delivery conduit and bag-set wherein the bag set comprising a tubing assembly, a separation assembly, and a filter assembly. Methods of using the system are also disclosed.

26 Claims, 5 Drawing Sheets

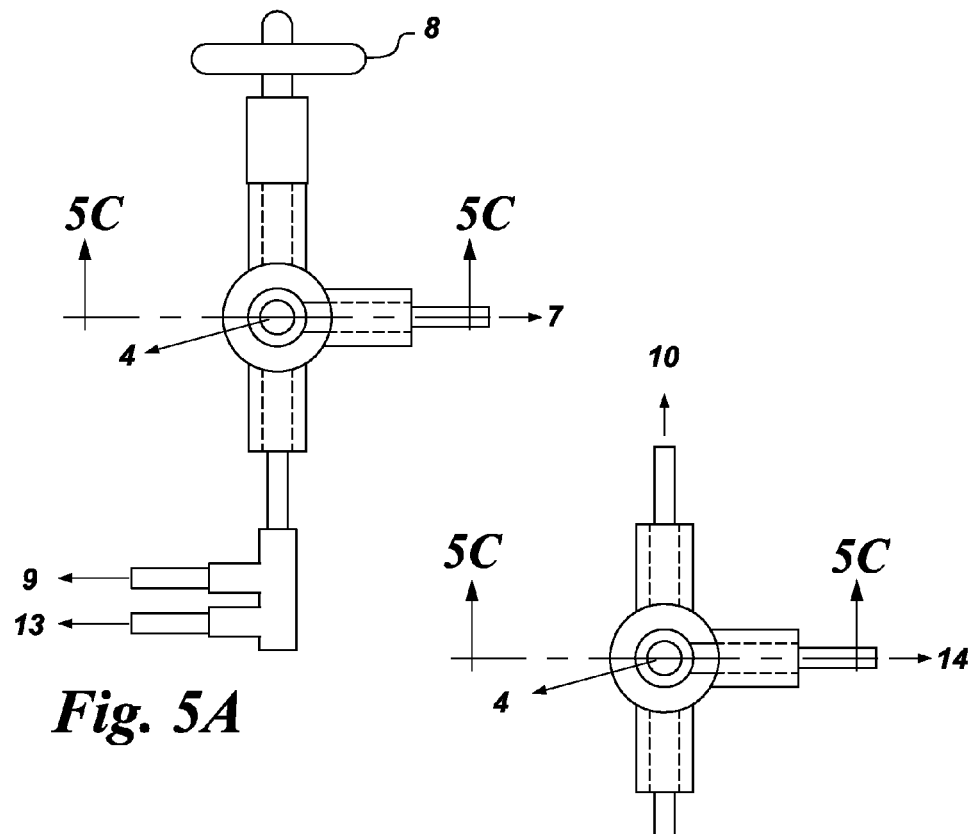
Fig. 5A
Fig. 5B
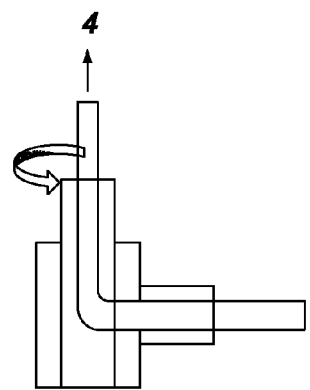
Fig. 5C

DISPOSABLE FLUID PATH SYSTEMS AND METHODS FOR PROCESSING COMPLEX BIOLOGICAL MATERIALS

BACKGROUND

Many conventional blood cell isolation procedures require preliminary red blood cell depletion and sample volume reduction. These are commonly required processing steps for long-term cell banking and regenerative medicine applications where a maximal yield of rare cells is desired in a reduced volume due to storage limitations and/or the small volume requirements needed for direct transplantation. Today, the most common techniques for processing blood-cell containing samples (e.g. cord blood, bone marrow, peripheral blood) involve density-gradient sedimentation using centrifugation with or without the use of a density-gradient media to improve separations. Automated centrifugal systems have recently been developed for closed-system processing of cord blood and bone marrow samples in order to meet the growing needs for high-throughput sample processing. While greatly improving throughput compared to manual techniques, centrifugation-based devices have limited flexibility and portability due to the weight and fixed physical dimensions of the centrifuge bucket.

Thus there is a need for design simplification that would address issues related to a centrifuge process that will allow high cell recovery.

BRIEF DESCRIPTION

The invention is adapted to address the need for a functionally-closed bag set system for filtration-based concentration of particular target cells (e.g, stem cells), wherein the target cells are some fraction of the input biological sample (e.g., cord blood).

In one embodiment a gravity assisted disposable system for separating a biological sample into two or more distinct submaterials through sedimentation is disclosed comprising a sample delivery conduit; and a bag-set in fluid communication with the sample delivery conduit and wherein said bag-set is a functionally-closed fluid path. The bag-set comprises a tubing assembly for transferring the biological material through the bag-set, separation assembly in fluid communication with the tubing assembly configured to receive the biological sample from the sample delivery conduit and to allow for sedimentation of a submaterial from the biological material; and a filter assembly in fluid communication with the tubing assembly and the separation assembly. The filter assembly is configured to; receive the biological material and at least one submaterial from the separation assembly through the tubing assembly for filtering and to return retentate material to the separation assembly through a retentate conduit and deliver permeate material to the separation assembly through a permeate conduit.

In another embodiment a method for processing biological materials using the aforementioned system is disclosed. The method comprises the steps of adding a biological material to the system such that said material is transferred through the sample delivery conduit to the processing bag through a gravity feed, evacuating air from the storage system using pumping device, prewetting the filter unit by adding material into said filter unit from the supply bag, adding an aggregating agent from the storage unit to the processing bag and allowing the biological material to separate into a sedimentation material and a non-sedimentation material, transferring a portion of the sedimentation material through the tubing assembly into the supply bag, transferring the remaining material through the tubing assembly into the filter unit and returning retentate material to the processing bag through the retentate conduit and permeate material to the permeate bag through the permeate conduit until a predetermined level of retentate remains in collected in the processing bag, flushing the tubing assembly and filtration unit with permeate to remove retentate from the filtration unit; purging the tube assembly and filtration unit with air, and transferring the retentate material from the processing bag through the tube assembly into the storage unit.

DRAWINGS

These and other features, aspects, and advantages of the present invention will become better understood when the following detailed description is read with reference to the accompany figures.

FIG. 5 illustrates multi-port diverters that may be used for directing fluid flow within the bag-set; arrows depict the outlet to the specific bag-set components.

DETAILED DESCRIPTION

The invention relates generally to systems for processing complex biological materials into subcomponents. The invention addresses the need for a sterile single-use disposable fluid path system for processing of biological materials (e.g., whole blood, cord blood, etc.) while achieving high target-cell recoveries and viabilities. Typically, the biological materials are added to a specialized pre-sterilized disposable processing set through a sterile or aseptic method. The processing set is customized to function with a machine to manipulate the biological materials towards some end, such as, target cell isolation and/or sample concentration.

The systems of the invention generally comprise a disposable system for separating a biological sample into two or more distinct submaterials wherein at least one of the submaterials is separated through sedimentation. The sedimentation is gravity assisted, completed at 1 g, without the need for a centrifugal system. The system comprises a disposable closed fluid path bag-set in fluid communication with a sample delivery conduit. The sample delivery conduit is used in transferring the biological material to be processed from a collected sample receptacle to the closed fluid path bag-set.

A closed fluid path refers to a system for processing fluid whereby once material enters the system it is isolated until processing is completed. "Closed system" in the present invention refers to the biological material entering the fluid path bag-set and being isolated within the components of the bag set until aggregation and filtration is completed. Additionally, a "closed system" for processing biological fluids typical implies that all internal portions fluid path and connected components are sterile. The term "functionally-closed system" further implies that the closed fluid path can have inlet and outlet ports for the addition of fluid or air yet sterility is maintained with the use of filters (e.g., 0.2 um membrane) at each port.

Figure 1:
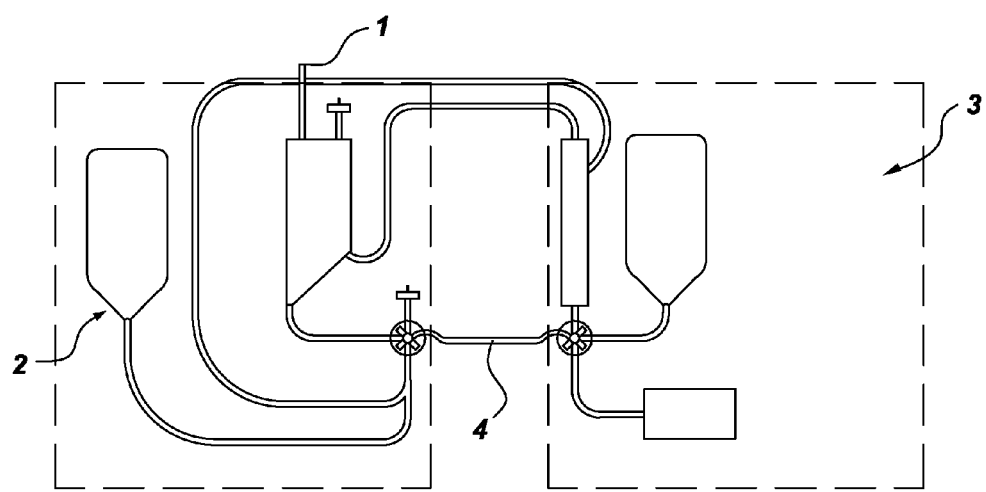
FIG. 1 is a schematic representation of one embodiment showing a disposable closed bag-set.
Figure 2:
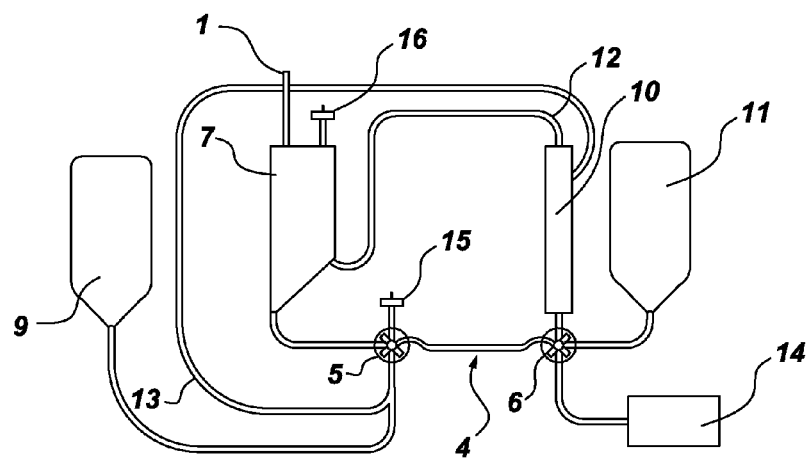
FIG. 2 is a schematic representation of the individual components of the disposable closed bag set.

The disposable functionally-closed bag-set is designed for filtration-based concentration of particular target cells, for example stem cells, wherein the target cells are some fraction of the input biological material (e.g., cord blood). To accomplish the filtration-based concentration, the bag-set has an architecture composed of various components. One embodiment is shown in FIG. 1 and includes a sample delivery conduit 1, separation assembly 2, filter assembly 3, and tubing assembly 4. The dimension and geometry of the bag-set may vary based on the application A more detailed is a schematic representation of the disposable functionally-closed bag-set is shown in FIG. 2. As shown, a disposable functionally-closed system for separating a biological sample into two or more distinct submaterials may be comprised of a tube assembly 4 having an intake-valve subassembly 5 on a first end and a filter-valve subassembly 6 on a second end. The combination of the tube assembly, intake-valve subassembly, and filter-valve subassembly is used to control flow of material through the separation assembly and filter assembly as shown earlier in FIG. 1.

The intake-valve subassembly may be a multi-port diverter valve comprising a first port in two-way fluid communication with a processing bag 7. The processing bag is configured to receive a biological sample from the sample delivery conduit 1 and to allow for sedimentation of the material. A second port of valve 5 is in two-way fluid communication with a permeate bag 9. The permeate bag is configured to receive permeate from a filtration unit 10 which is part of the filtration assembly.

As shown, a third port of the intake-valve subassembly may be used for fluid communication with a filter membrane 15. The filter membrane, which also may contain a check valve, is configured to allow air or gas into the system. The intake-valve assembly 5 has a fourth and final port in two-way fluid communication with the tubing assembly 4. In certain embodiment, the valve may be configured so that a fourth port can be connected to the other three ports to divert the flow of fluid in either direction.

Referring further to FIG. 2, the filter-valve subassembly 6 may be a multi-port diverter comprising a first port in two-way fluid communication with a supply bag 11. The supply bag is configured to supply an aggregating agent to a processing bag and to receive waste sediment materials from the separation assembly portion of the system. The filter-valve subassembly has a second port in fluid communication with a filtration unit 10. The filter is configured to filter a solution containing the biological sample and return retentate material to the processing bag 7 through a retentate conduit 12 and permeate to the permeate bag 9 through a permeate conduit 13. In certain embodiments, the filtration unit may be a hollow fiber filter.

As shown in FIG. 2, the retentate conduit 12 is connected to the processing bag 7 through a side port. The side port may be positioned tangential to an asymmetric funnel shaped lower portion of the processing bag. The permeate conduit has a first end connected to the outlet end of the filtration unit 10 and a second end connected to a location between the permeate bag 9 and the intake-valve subassembly 5. The location is to minimize trapped air within the line.

The filter-valve assembly is also configured to have a third port that is in two-way fluid communication with a storage unit 14. The storage subassembly is configured to receive a submaterial, which may be a retentate. The filter-valve assembly 6 has a fourth and final port in two-way fluid communication with the tubing assembly 4. The valve is configured so that fourth port may be connected to the other three ports to divert the flow of fluid in either direction.

The bag-set may be designed for compatibility with a wide working volume range depending on the biological material to be processed. In certain embodiments, the input sample range may be approximately 50-300 mL, the processing bag, supply bag, and permeate bag working volume maximum is approximately 1 L. However, the size of the various bags is not limited and may be adjusted based on the sample and sample size of interest. Further, the various components of the bag-set may be designed to further enhance separation and aid in cell recovery.

In certain embodiments, a biological fluid (e.g., cord blood) may be added to the disposable bag-set using the sample delivery conduit. The sample delivery conduit is designed to allow gravitational transfer of the sample into the bag-set while maintaining sterility and preventing loss of sample. The connection between the biological material receptacle and the sample delivery conduit may be accomplished using a variety of techniques including, but not limited to, inline tube welding for a sterile tube-to-tube connection, aseptic methods such as a transfer spike or a luer-to-luer connection (e.g., a syringe luer). The biological material may then be gravity drained through the sample transfer subassembly into the processing bag. In certain embodiments, the biological material may be transferred using an external peristaltic pump.

Figure 3:
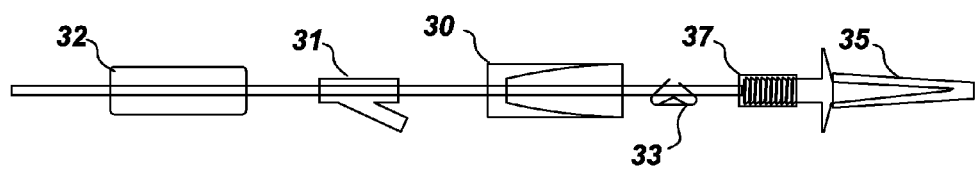
FIG. 3 is a schematic representation of a sample delivery conduit.

FIG. 3 is a schematic representation of a sample delivery conduit using an aseptic transfer spike 35 with a luer connection 37. As shown additional components may be added to the conduit to facilitate operations. The components may include, but are not limited to a clot-filtering device 30, an accessible sample port 31, a sample pillow chamber 32, and additional fixation points and clamps 33.

The processing bag may be designed to hold a given three-dimensional shape even when empty and to allow air to escape as fluid fills the internal volume of the processing bag. In one embodiment, this is accomplished by using a hydrophobic in-line filter with one side open to air. In other embodiments an inert gas may be used in place of the filter air. Air vents or ports are required for air balance and line purging, however the amount of air entering the system is minimized and sterility within the system may be maintained. Thus, even though air does enter or exit, the system during processing, the bag-set may still be defined as a functionally closed system, so long as the air entering the system is filtered or sterilized. In certain embodiments a 0.2 um filter may be used.

Figure 4:
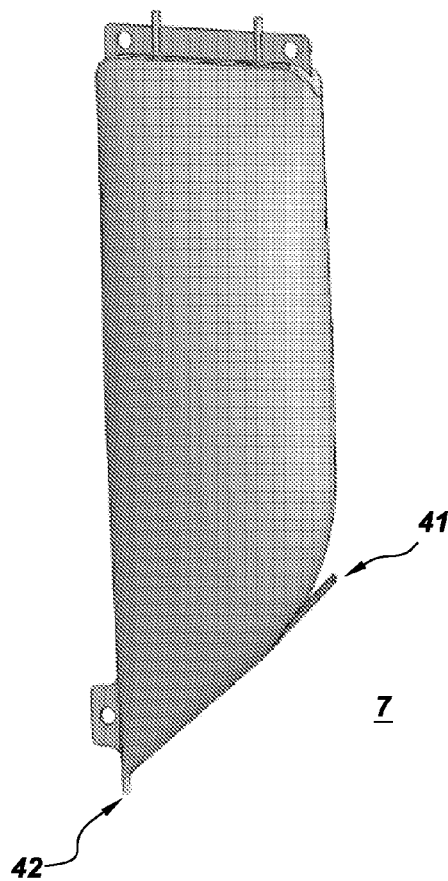
FIG. 4 is a schematic representation of a processing bag.
Figure 6:
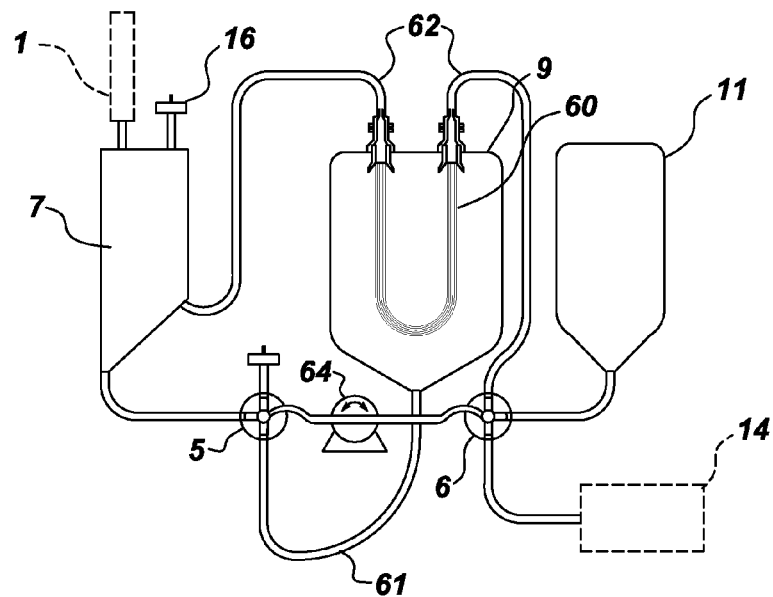
FIG. 6 is a schematic representation of one embodiment showing a hollow fiber filter is disposed within the permeate bag.

The design of the processing bag may enable high recoveries of target cells and sample collection from an aggregation enhanced filtration-based concentration process. One embodiment is shown in FIG. 4 where the processing bag is oblong with an asymmetric funnel shape at the bottom. In certain embodiment, the bag may be a blow-molded structure, which gives the bag some three-dimensional shape. A three-dimensional shape may be used to prevent the two sides of the bag to collapse towards each other during drainage (as a typical two-ply seam sealed bag would do). The smooth funnel shape at the bottom of the processing bag may prevent or reduce the collected aggregated material from separating during drainage (e.g., when the collected material is red blood cells).

In certain embodiments, the processing bag may be designed such that the volume of the aggregated material is less than the volume of the funnel portion of the bag. The angle of the funnel may also be controlled. With a high angle, relative to the horizontal when the oblong bag is vertical, on the funnel shape, the aggregated material can typically be pumped out quickly without breaking up. However, a very high angle will tend to prevent the biological material from reaching the maximum aggregation density in a given amount of time as a high angle essentially creates a narrow tube that limits settling.

At the top of the asymmetric funnel (7), a side port (41) may be connected to the bag. The side port may be tangent to the slope of the funnel. During the filtration process, fluid is pumped out of the bottom port (42), through the filter, and the retentate is returned through the side port while permeate material flows into the permeate bag. As the fluid level in the processing bag drops below the level of the side port during the filtration process (concentration), the retentate enters the side port. As such, the returning retentate should not significantly disturb the level of the fluid or cause foaming.

Level sensing of the fluid may be used to determine the final sample collection volume or the concentration factor from filtering. In certain embodiments a level sensor is an optical sensor using through transmission or reflectance. In certain embodiments level measurements may be accomplished using an ultrasound or capacitance sensor. If the level is significantly disturbed or if foaming occurs, the optical sensor (near the bottom port of the bag) may give a false level reading. The side port is also strategically placed. If the side port and the exit port are placed close together then filtering effectiveness may be decreased due to short-circuiting of the fluid path. If the side port is located a large distance away from the exit port, the size of the bag becomes impractical for blow molding.

In certain embodiments, the processing bag may also comprise a filter membrane 16 to allow air out of the system. A check valve may also be used and positioned between the filter membrane and the processing bag. The filter membrane is shown in FIG. 2.

In other embodiments, sensors may also be used to monitor or measure materials throughout the bag-set.

FIG. 5 illustrates a multi-port diverter valve that may be used for directing fluid flow within the fluid path when the tubing assembly is integrated with a pumping device. The arrows, in FIG. 5, depict the connection of the various ports to the components of the bag-set as shown earlier in FIG. 2. The multi-port diverter valves may be used in both the intake-valve subassembly 5A and the filter-valve subassembly 5B. Also shown is a cross sectional view 5C. The valves may be four port valves that are designed to control the flow between one port (the port connected to a pumping loop) and the three additional ports. The valve may also prevent fluid from flowing between any of the ports (in the off position).

The fluid flow can be in either direction through the connected ports. In certain embodiments, one or both of the valve subassemblies may be comprised of more than one valve arranged in series or in parallel wherein the one or more valves are designed to direct the flow between the various components.

Referring again to FIG. 2, in certain embodiments, the intake-valve subassembly connects the tubing assembly to the processing bag, the permeate collection bag, and an air filter/check-valve. The air filter/check valve is used for purging of the lines. The filter-valve subassembly connects the tube assembly to the supply bag, the filtration unit, and the storage unit.

In certain embodiments, an in-line pump, such as a peristaltic pump, may be used and integrated with the tube assembly. The peristaltic pump is configured to externally manipulate fluid within the tube without directly contacting the fluid and is positioned between the intake-valve subassembly and the filter-valve subassembly. In certain configuration with the multi-diverter valves open, the pump is able to move fluid and air through a large number of different fluid path configurations. Thus with the engagement of only two valves and a pump loop, the necessary process steps for aggregation enhanced filtration-based concentration may be accomplished.

In certain embodiments, the multi-valve diverter valves are stopcocks, which may be used instead of a pinch valve manifold. A pinch valve manifold to replicate the function of a four port stopcock arranged in a manner taught above would require at least three tube-pinching units. There is some difficulty in arranging the pinch units closely together given the typical sizes of the actuators or mechanism required. Thus, a pinch valve manifold would typically have much higher dead volumes or hold-up volumes, thus potentially reducing final recoveries.

In certain embodiments, the permeate bag is configured as a receptacle for storing the permeate collected during filtration. In certain embodiments there may be an intermediate connection from the permeate bag to the four port intake-valve subassembly. This intermediate connection may allow for the intake-valve to draw fluid from the permeate bag without any air initially in the tubing.

In certain embodiments a cryogenic unit may be used as the storage unit. The cryogenic unit allows for cold storage of the collected sample. The cryogenic unit may be an integral part of the device. In other embodiments, the cryogenic unit may be remote from the closed bag-set wherein a transfer line is used to transfer the collected sample to the remote unit. In either embodiment, the cryogenic unit is capable of undergoing cryogenic freezing and is compatible with biological cryogenic preservatives.

As shown, the design of the functionally closed bag-set may allow the bag-set to be used in an aggregation and filtration process with a minimal number of interface components. Reducing the number of interface components and flow control may improve cell recovery and viability. In certain embodiments the components of the closed bag-set may be comprised of material that can be sterilized and which meets at least one of FDA and USP requirements for biocompatibility. This includes materials used in construction of the bags, tubing, valves, and connectors. Also included may be auxiliary components such as retention clips, sealants, and adhesives, which may come in contact with the materials undergoing filtration or processing.

Various components of the bag set may be configured to reduce the number and type of ancillary components needed or consolidate parts having similar functionalities. For example, in certain embodiments the filter assembly may be configured such that it is an integral part of one of the bag features: permeate bag, processing bag, or supply bag.

One such embodiment is shown in FIG. 6, wherein the filter subassembly is comprised of housingless hollow fiber bundles 61 which are disposed directly in a permeate bag 9. The flow inlet and outlet to the inner lumen of the hollow fibers are capped with a flow port that extends outside of the bag 62. As shown, the volume defined by the external surface of the hollow fiber filter and the inner surfaces of the permeate bag acts as the permeate conduit such that permeate is disposed directly in the permeate bag. FIG. 6 also shows a peristaltic pump integrated with the tubing assembly 64.

In one embodiment, wherein the filter fiber bundle 60 is disposed directly in the permeate bag 9 and the permeate conduit 61 is connected directly to the intake-valve subassembly, the conduit is a large diameter tubing. This would allow for the air to be displaced out of the permeate line.

Figure 7:
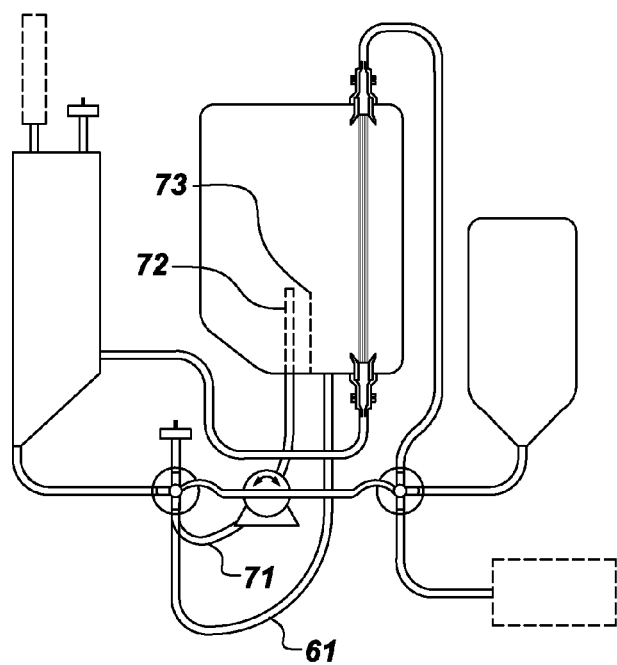
FIG. 7 is a schematic representation of one embodiment showing a hollow fiber filter is disposed within the permeate bag with the fibers in a vertical configuration.

In further embodiment shown in FIG. 7, wherein the filter fiber bundle is in a top-to-bottom linear configuration and disposed directly in the permeate bag, the permeate conduit may be branched near the intake-valve port with both portions of the conduit, 61 and 71, plumbed to the permeate bag. One line may have a periscope tube 72 extending a small way vertically into the bag. In this manner, the air in the line will be displaced as the bag fills up with permeate. After a short time as the bag continues to fill, both lines will be completely filled with permeate, which will allow the pump to draw in permeate without any air. In another embodiment, to allow for air displacement in the permeate conduit a small partial partition 73. The partial partition may be melt sealed into the bag or be a small physical divider. This would allow for the air to be displaced out of the permeate line 61.

In certain embodiments the functionally closed bag-set may be contained in a soft-tray is a multi-functional component that serves as a shipping and protective container. In certain embodiments the tray may also be design for 'drop-in' loading of the bag-set into a separate auxiliary system, which is designed for large volume throughput of sample filtration and processing. As such the tray may minimize handling, sorting, or positioning of the complex bag-set assembly into the apparatus. The tray may also act as a quality control device or guide to accurately positions components for engagement with the auxiliary system and maintain sterility.

In certain components, the tray may be designed to have seating structures on its internal surface. The structures would serve to position the various components of the bag-set in a manner to allow the components to engage with the auxiliary system in operation. In certain embodiments, the components that engage with the auxiliary system may be the intake-valve subassembly and the filter-valve subassembly. The tray may also be designed such that the tubing assembly may be accessible by a pumping device, exterior to the tray.

Figure 8:
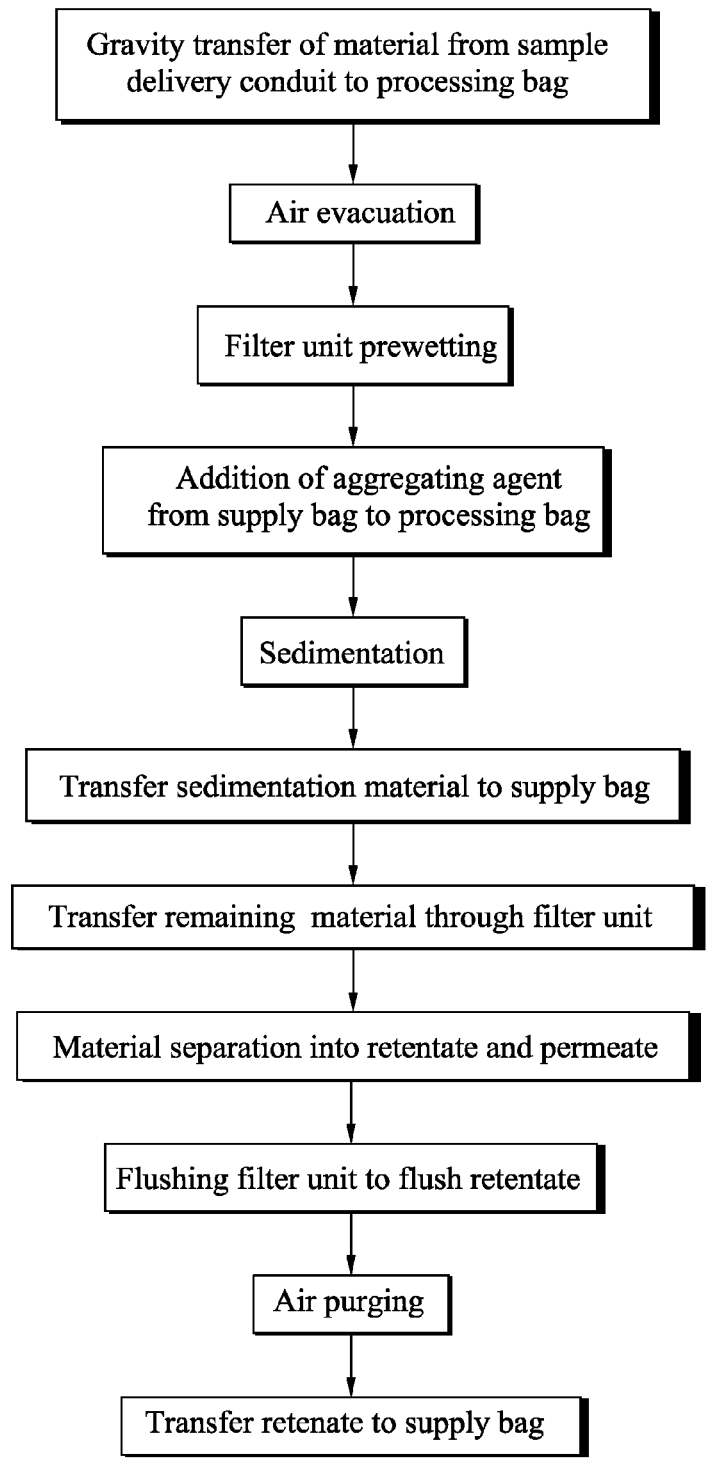
FIG. 8 is a flow chart depicting a process for using the disposable bag-set.

The design of the functionally closed bag-set may allow the bag-set to be used in an aggregation and filtration process in a closed fluid path with a minimum number of processing steps. FIG. 8 is a flow diagram showing one embodiment of the process. As shown in the first step, material may be transferred from the sample delivery conduit to the processing bag using gravitational feed. Air is evacuated from the system, more specifically from the storage unit to avoid air entrapment and over inflation of a fixed volume storage unit. The filter unit may be prewetted by addition of the aggregating agent, stored in the supply bag in a stepwise fashion by cycling the flow of the material using a peristaltic pump. The aggregating agent may then be transferred to the processing bag for mixing with the biological sample. The sample is allowed to segregate through sedimentation. This may be accomplished without the operation of the pump.

After sedimentation, the sediment material may be transferred to the supply bag through the tubing assembly. Material remaining in the processing bag may then be moved through the tubing assembly into the filter unit. The filter processes the material and seperates it into a retentate and a permeate. Retentate material is returned to the processing bag through the retentate conduit. Permeate material is returned to the permeate bag through the permeate conduit.

The retentate material returned to the processing bag may be re-circulated through the filter unit multiple times. Material is transferred into the filter unit until a predetermined level of retentate remains in the processing bag. An optical sensor may be used to determine the level wherein the optical sensor is configured to identify a material interface.

Material may be transferred from the permeate bag through the tubing assembly and filtration unit to remove a remaining retentate by flushing. Flushing with a low viscosity permeate may be desired due to viscosity changes of the material wherein the retentate may be highly viscous. Additionally, the flushing may be desired to recover the maximum amount of filtered material from the filter unit and connected tubing. The tube assembly and the filtration unit may be flushed with air, and the desired retantate material transferred from the processing bag through the tube assembly to the storage unit.

Table 1 further illustrates the process and shown valve positioning and direction of the integrated pump for each step in the process. As shown in the table material moves in each of the process step between the components identified, and in the direction shown by the pump setting. If the pump direction is shown as forward, material moves in the direction of intake-valve to filter-valve. If the pump direction is reverse, material moves from filter-valve to intake-valve. For example in step 4, aggregating material moves from the supply bag to the processing bag, the pump is set to operate in the reverse direction.

TABLE 1

Valve positioning and Directional Flow of Process Steps

| Process Step | Intake-valve subassembly | Filter-valve subassembly | Pump Direction |
|---|---|---|---|
| 1 | Closed | Closed | Off |
| 2 | Permeate bag | Storage unit | Reverse |
| 3 | a. Permeate bag<br>b. Filter membrane | a. Supply bag<br>b. Filter unit | a. Reverse<br>b. Forward |
| 4 | Processing bag | Supply bag | Reverse |
| 5 | Closed | Closed | Off |
| 6 | Processing bag | Supply bag | Forward |
| 7 | Processing bag | Filtration unit | Forward |
| 8 | Processing bag | Filtration unit | Forward |
| 9 | Permeate bag | Filtration unit | Forward |
| 10 | Air-intake | Filtration unit | Forward |
| 11 | Processing bag | Storage unit | Forward |

The various systems and methods of filtration described may be used in connection with the system and methods described in U.S. patent application Ser. No. 12/325,672, entitled SYSTEMS AND METHODS FOR PROCESSING COMPLEX BIOLOGICAL MATERIALS and U.S. patent application Ser. No. 12/635,231, entitled METHODS FOR MAKING A HOUSINGLESS HOLLOW FIBER FILTRATION APPARATUS, which are hereby incorporated by reference.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A gravity assisted disposable apparatus for separating a biological sample into two or more distinct submaterials through sedimentation comprising:
    a sample delivery conduit; and
    a bag-set in fluid communication with the sample delivery conduit and wherein said bag-set is a functionally-closed fluid path comprising;
        a tubing assembly for transferring the biological material through the bag-set;

a separation assembly in fluid communication with the tubing assembly configured to receive the biological sample from the sample delivery conduit and to allow for sedimentation of a submaterial from the biological material; and a filter assembly in fluid communication with the tubing assembly and the separation assembly, wherein said filter assembly is configured;

to receive the biological sample and at least one submaterial from the separation assembly through the tubing assembly for filtering;

to return retentate material to the separation assembly through a retentate conduit;

to deliver permeate material to the separation assembly through a permeate conduit; and to return permeate material from the separation assembly to said filter assembly through the tubing assembly.

2. The apparatus of claim 1 wherein the separation assembly comprises:

an asymmetrical three dimensional processing bag having an oblong shaped upper portion and a funnel shaped lower portion wherein at least a portion of interior walls of said processing bag maintains separation during drainage of the biological sample and wherein the lower portion of said bag is sufficiently transparent to allow optical sensing;

an inlet port attached to the processing bag for receiving the biological sample from the sample delivery conduit;

a side port attached tangentially to the asymmetric funnel shaped lower portion of the processing bag for the delivery of a retentate from a retentate conduit;

a bottom port attached to the bottom portion of the processing bag from removing the biological sample from the processing bag; and a permeate bag a configured to receive permeate solution from the filter assembly through a permeate conduit.

3. The apparatus of claim 2 wherein the processing bag further comprise fixture points to align the bag with an optical sensor.

4. The apparatus of claim 2 wherein the processing bag is aligned for sedimentation such that the oblong shaped upper portion vertically positioned above the funnel shaped lower portion.

5. The apparatus of claim 2 wherein the processing bag further comprising a filter membrane configured to allow air into or out of the system.

6. The apparatus of claim 5 further comprising a check valve positioned between the membrane filter and the processing bag.

7. The apparatus of claim 1 wherein the filter assembly comprises:

a hollow fiber filtration unit in fluid communication with the tubing assembly for filtering the biological sample and returning retentate material to a processing bag through the retentate conduit and permeate material to a permeate bag through the permeate conduit;

a supply bag in fluid communication with the tubing assembly and configured to supply an aggregating agent to a processing bag and to receive waste aggregate from the separation assembly; and a storage unit in fluid communication with the tubing assembly and configured to receive a submaterial from the separation assembly.

8. The apparatus of claim 7 further comprising an in-line frangible connector situated between the supply bag and the tubing assembly.

9. The apparatus of claim 6 wherein the storage unit is comprised of material capable of undergoing cryogenic freezing and is compatible with biological cryogenic preservatives.

10. The apparatus of claim 7 wherein the hollow fiber filtration unit is disposed within a permeate bag, said permeate bag being a component of the separation assembly and wherein the permeate conduit is the external surface of the hollow fiber filtration unit.

11. The apparatus of claim 10 wherein the permeate bag further comprises a periscope tube, a partial partition, or a combination thereof.

12. The apparatus of claim 1 wherein the tubing assembly comprises a first end in fluid communication with an intake-valve subassembly and a second end in fluid communication with a filter-valve assembly, said tubing assembly configured to be integrated with a peristaltic pump such that the peristaltic pump externally manipulates fluid within the tube without directly contacting the fluid, and wherein:

the intake-valve subassembly is a multi-port diverter comprising a port connected to the processing bag and a second port connected to the permeate bag; and the filter-valve subassembly is a multi-port diverter comprising a first port connected to the hollow fiber filtration unit, a second port connected to the supply bag, and a third port connected to the storage unit.

13. The apparatus of claim 12 wherein the multi-port diverters control flow with a non-pinch seal device.

14. The apparatus of claim 13 wherein the non-pinch seal device is a stopcock, a diagram valve, a butterfly valve, a ball valve, or a combination thereof.

15. The apparatus of claim 12 further comprising a membrane filter in fluid communication with the intake-valve subassembly and configured to allow air into the system.

16. The apparatus of claim 15 further comprising a check valve positioned between the membrane filter and intake-valve subassembly.

17. The apparatus of claim 12 wherein the permeate conduit of the separation assembly is in fluid communication with a port of the intake-valve subassembly.

18. The apparatus of claim 1 wherein the sample delivery conduit comprises a transfer spike, a luer-to-luer connection, a section for in-line tube welding, or a combination thereof.

19. The apparatus of claim 1 wherein the biological material is whole blood, cord blood or bone marrow.

20. The apparatus of claim 1 wherein the submaterial comprises blood cells, leukocytes, stem cells, nucleated cells or a combination thereof.

21. The apparatus of claim 1 wherein said system further comprises sensors for measuring at least one of fluid levels or pressure within the system.

22. The apparatus of claim 21 wherein the sensors comprise, pressure, optical, capacitive, or a combination thereof.

23. The apparatus of claim 1 further comprising a tray assembly, said tray assembly for positioning the assemblies of the system into a predetermined configuration.

24. The apparatus of claim 23 wherein the predetermined configuration is for at least one of quality control, protecting the subassemblies during movement, and facilitating engagement with an auxiliary system.

25. The apparatus of claim 23 wherein the tray further comprises a plurality of seating structures for positioning components of the bag-set to allow engagement of said components with an auxiliary system.

26. The apparatus of claim 25 wherein the components are an intake-valve subassembly and a filter-valve subassembly.

* * * * *